(12) United States Patent
Drevillon et al.

(10) Patent No.: US 7,196,792 B2
(45) Date of Patent: Mar. 27, 2007

(54) LIQUID CRYSTAL BASED POLARIMETRIC SYSTEM, A PROCESS FOR THE CALIBRATION OF THIS POLARIMETRIC SYSTEM, AND A POLARIMETRIC MEASUREMENT PROCESS

(75) Inventors: Bernard Drevillon, Clamart (FR); Antonello De Martino, Montrouge (FR)

(73) Assignees: Centre National de la Recherche Scientifique (CNRS), Paris Cedex (FR); Ecole Polytechnique, Palaiseau Cedex (FR)

( * ) Notice: Subject to any disclaimer, the term of this patent is extended or adjusted under 35 U.S.C. 154(b) by 383 days.

(21) Appl. No.: 10/684,361

(22) Filed: Oct. 15, 2003

(65) Prior Publication Data

US 2004/0130717 A1 Jul. 8, 2004

(30) Foreign Application Priority Data

Oct. 15, 2002 (EP) .................................. 02292544

(51) Int. Cl.
 *G01J 4/00* (2006.01)
(52) U.S. Cl. ...................................... 356/367; 356/369
(58) Field of Classification Search ................ 356/364, 356/367, 369; 250/559.09, 225
 See application file for complete search history.

(56) References Cited

U.S. PATENT DOCUMENTS 4,523,848 A * 6/1985 Gorman et al. ............. 356/368

5,521,705 A * 5/1996 Oldenbourg et al. ........ 356/368
6,175,412 B1 * 1/2001 Drevillon et al. ........... 356/369
6,552,836 B2 * 4/2003 Miller ........................ 359/237

FOREIGN PATENT DOCUMENTS

FR 2 755 254 4/1998

OTHER PUBLICATIONS

November L J et al: "Liquid Crystal Polarimeter: A Solid State Imager for Solar Vector Magnetic Fields", Optical Engineering, Soc. of Photo-Optical Instrumentation Engineers. Bellingham, US, vol. 34, No. 6, Jun. 1, 1995, pp. 1659-1668, XP000511328, ISSN: 0091-3286 *abstract*, *p. 1661, col. 1, paragraph 1—col. 2, paragraph 1*.

* cited by examiner

*Primary Examiner*—Gregory J. Toatley, Jr.
*Assistant Examiner*—Roy M. Punnoose
(74) *Attorney, Agent, or Firm*—Young & Thompson (57) ABSTRACT

A liquid crystal based polarimetric system, a process for the calibration of this polarimetric system, and a polarimetric measurement process intended for measuring the representative parameters of a sample in which the polarimetric system contains an excitation section emitting a light beam that passes through a polarization state generator (PSG) and onto a sample. After reflection or transmission by the sample, the beam goes through an analysis section with a polarization state detector (PSD). The PSG and PSD each have a first and a second liquid crystal elements $LC_j$ (j=1,2) having, for each $LC_j$ element of the PSG (respectively for each $LC_j$ element of the PSD), an extraordinary axis making an angle $\theta_j$ (resp. $\theta'_j$) with respect to the polarization direction (i), and a retardation $\delta_j$ (resp ($\delta'_j$)) between its ordinary and extraordinary axes, the liquid crystals $LC_j$ elements being positioned in reverse order in the PSD with respect to the $LC_j$ elements of the PSG.

21 Claims, 4 Drawing Sheets

LIQUID CRYSTAL BASED POLARIMETRIC SYSTEM, A PROCESS FOR THE CALIBRATION OF THIS POLARIMETRIC SYSTEM, AND A POLARIMETRIC MEASUREMENT PROCESS

BACKGROUND OF THE INVENTION

The invention relates to a liquid crystal based polarimetric system for analyzing a sample, a process for the calibration of this polarimetric system and a polarimetric measurement process.

DESCRIPTION OF THE RELATED ART

In order to measure parameters which are representative of a sample (for example, of its composition and thickness), it is conventional to make use of an ellipsometer.

Ellipsometry is a powerful non invasive probe in which reflectance or transmittance data are measured by electromagnetic radiation outcoming from a sample. Briefly, the surface of a studied sample is illuminated by a photon beam that is reflected or transmitted and the polarization state of the outcoming beam is compared to that of the incident beam.

This conventional ellipsometry method proves satisfactory when the reflected light is still totally polarized (even though elliptically), which is indeed the case, among other examples, for isotropic layers with smooth interfaces. Such samples, which can be considered as "dichroïc retarders" (DR) are usually characterized by the ellipsometric angles $(\Psi, \Delta)$ defined by $$r_p/r_s = \tan(\Psi)\exp(i\Delta) \quad (1)$$

where $r_p$ and $r_s$ are respectively the amplitude reflectivities of the sample for linear polarizations in the incidence plane ($r_p$), or perpendicular to this plane ($r_s$).

However, to study samples that cannot be described as DRs, such as partially depolarizing materials, a more general method is required.

Polarimetric systems enable to measure all the polarization components of light in any sample.

The polarization state of light can be represented in the most general case by a four-dimensional vector, called the Stokes vector (S).

A description of this can be found in the work of Azzam and Bashara entitled "Ellipsometry and polarized light", North-Holland, pp. 55–60.

The Stokes vector consists of the I, Q, U and V coordinates. I stands for the total intensity, while the other components are defined as the differences between the intensities measured through different pairs of "complementary" polarizers (linear polarizers set vertical and horizontal for Q, at +45° and −45° azimuthal angles for U, and left and right circular polarizers for V).

The interaction of light with any sample can then be represented by a matrix, so-called, the Mueller matrix, of dimensions 4×4 with therefore 16 real coefficients.

The extraction of the 16 parameters during polarimetric measurements provides a complete characterization of the said medium.

For a DR characterized by ellipsometric angles $(\Psi, \Delta)$ (see eq. (1)) the Mueller matrix elements are the following:
upper diagonal block $$M_{11}=M_{22}=\tau, \ M_{12}=M_{21}=-\tau\cos(2\Psi)$$

lower diagonal block $$M_{33}=M_{44}=\tau\sin(2\Psi)\cos(\Delta), \ M_{34}=-M_{43}=\tau\sin(2\Psi)\cos(\Delta) \quad (2)$$

other elements: $M_{ij}=0$ where the additional parameter $\tau$ is proportional to the overall intensity transmission or reflection coefficient of the sample. We point out that this Mueller matrix has
two real eigenvalues: $(\lambda_{R1}=2\tau\sin^2(\Psi), \lambda_{R2}=2\tau\cos^2(\Psi))$, and two complex conjugate eigenvalues:

$$(\lambda_{C1}=\tau\sin(2\Psi)\exp(i\Delta), \ \lambda_{C2}=\tau\sin(2\Psi)\exp(-i\Delta)). \quad (3)$$

Many designs have been proposed, and demonstrated, for Mueller polarimetric systems. All of them comprise a polarization state generator (PSG) which modulates the Stokes vector ($S_{in}$) of the light impinging on the sample and a polarization state detector (PSD) which analyzes the polarization ($S_{out}$) of the light outcoming from the sample. It is customary to define the modulation matrix W as a 4×4 real matrix whose columns are the four Stokes vectors $S_{in}$ generated by the PSG. Reciprocally, the four dimensional signal vector D eventually delivered by the PSD is related to the Stokes vector $S_{out}$ of the light outcoming from the sample by a linear relationship D=A$S_{out}$, where A is the (4×4 real) analysis matrix representing the PSD. A raw measurement actually consists of 16 values of the signal, which form a matrix B=AMW, where A and W are respectively the analysis and modulation matrices defined above, and M the Mueller matrix of the sample. If A and W are known, M can be extracted from the raw data B as M=A$^{-1}$BW$^{-1}$. The determination of A and W is called calibration of the polarimeter. Clearly, the instrument must be designed in such a way that A and W are non singular. Moreover, in order to optimize error propagation from the raw measurement B to the final result M, the analysis and modulation matrices A and W must be "as close as possible" to unitary matrices. The best criterion in this respect is to optimize their condition numbers s(A) and s(W), which are the ratios of the smallest over the largest of their singular values {see for example Press W. H., Teukolsky S. A., Vetterling W. T. and Flannery B. P.; Numerical Recipes in Fortran, Cambridge University Press, p 53, who actually define the condition number as the reciprocal of that defined here; see also Compain E. and Drévillon B.; Rev. Sci. Instrum. 69, (1998) 1574}.

In a PSG, the light polarization can be modulated by a variety of devices such as discrete components inserted and then removed from the light path {Bickel W. S. et al.; Am. J. Phys 53 (1984) 468}, rotating retardation plates {Goldstein D. H.; Appl. Opt. 31 (1992) 6676}, rotating compensators {Collins R. W. and Koh J.; J. Opt. Soc. A 16, (1999) 1997}, Pockels cells {Delplancke F.; Appl. Opt. 36 (1997) 5388 and Compain E. and Drévillon B.; Rev. Sci. Instrum. 68 (1997) 2671} or photoacoustic modulators {Compain E. and Drévillon B.; Rev. Sci. Instrum. 69, (1998) 1574}. For PSD, one can use the same devices and a single detector, or a "parallel" analysis of light polarization through polarization-sensitive beamsplitters and simultaneous measurement of the separated beams by several detectors {Azzam R. M. A., Opt. Acta 29 (1982) 685, Brudzewski K.; J. Modern Optics 38 (1991) 889, Khrishnan S.; J. Opt. Soc. Am A 9 (1992) 1615, Compain E. et al., Thin Solid Films 313 (1998)}.

This variety of designs leads to a variety of characteristics, some of which are not compatible with each other; for example, high frequency polarization modulation by resonant devices such as photoelastic modulators allows efficient rejection of low-frequency noise, but for imaging applications by slow detectors such as typical Charge Coupled Devices (CCD), a stroboscopic illumination is then needed. Another important requirement for imaging applications is that the polarimetric elements exhibit large enough acceptance angles together with small enough aberrations. As a result, the devices which best meet these requirements are those based on low order retarding plates, which are either rotated {Pezzaniti J. L. and Chipman R. A., SPIE proceedings 2297 (1994) 468} or inserted and removed between sequential measurements, or those based on liquid crystal (LC) variable retarders.

Liquid crystal cells (LC) are electrically controlled low order retardation plates. Two types of such devices are currently available. First, nematic liquid crystals (NLC) provide variable retardation with fixed orientation of slow and fast axes, with typical response times of the order of 10 to 100 ms. On the other hand ferroelectric liquid crystals (FLC) provide fixed retardation, but with slow and fast axis directions which can be electrically switched between two azimuthal angles separated by 45°, in times typically shorter than 100 µs.

These elements provide non resonant polarization control which is naturally well suited for polarimetric imaging by a CCD. Therefore, devices comprising liquid crystal cells have been proposed for polarimetric imaging within the frame of conventional ellipsometry, i.e. for samples behaving as DR {Oldenbourg R. et al.; J. Microscopy 180 (1995) 140} and led to commercially available devices (Pol-Scole, by CRI, Inc. Boston).

Stokes polarimetry, i.e. polarimetry performed using a sole polarization state detector and no polarization state generator has also been performed, essentially in solar astronomy. The device consisted of two nematic LCs followed by a linear polarizer {Hofmann A.; SPIE proceedings 4133 (2000) 44} or even more complex assemblies, including for example two ferroelectric LCs, two fixed $\lambda/8$ retardation plates and a linear polarizer {Gandorfer A. M.; Opt. Engineering 38 (1999) 1402} or one ferroelectric, two nematic LCs and two quarter wave retardation plates {November L. J. and Wilkins L. M.; SPIE proceedings 2265, 210}.

An imaging Mueller polarimeter has been realized by using nematic LC cells {Bueno J. M.; J. Opt. A: Pure and Applied Optics 2 (2000) 216}. In this device, the PSG and PSD have the same design: each of them consists of one LC and one quarter-wave plate, the latter being mechanically inserted in and removed from the light path between acquisitions of raw images. This device has been used for polarimetric imaging of human eye, including retina and cornea.

However, the Mueller polarimeters described above, suitable for polarimetric imaging by slow devices such as CCDs, present two significant shortcomings.

First, their operation involves mechanical motion of optical elements, which are either rotated or moved in and out of the light path.

Second, their calibration relies on the characterization of individual optical components (polarizers and retardation plates). As a result, the accuracy of the overall calibration of the polarimeter is limited by the accumulation of the errors on the knowledge of each of those components, and on their positions. Furthermore, the instrumental configurations are most frequently defined in such a way that the polarization states generated by the PSG, or those "filtered" by the PSD are "simple" polarization states, such as linear (vertical and horizontal) and circular states, to reduce "cross-talk" and facilitate the overall calibration of the system. These "simple" configurations are far from those providing the highest values of s(A) and s(W), implying that for a given input noise on the raw data (B), the noise on the final result (M), is far from being optimized.

SUMMARY OF THE INVENTION

A purpose of the present invention is to remedy the shortcomings mentioned above and to propose a polarimetric system having one or more of the following features and advantages: namely, polarization modulation by liquid crystals only, with no mechanically moving parts, providing a wide enough acceptance angle for typical imaging applications, a simple and compact design including optimization with respect to error propagation, and a fast data acquisition, to be usable for measurements in real time.

Another purpose of the present invention is to provide two measurement processes, which can be used on the same instrument, and which yield:

In a simplified operation mode: the classical ellipsometric angles ($\Psi$, $\Delta$) of a sample assumed to be a DR. In addition, the validity of this assumption (which depends on the sample homogeneity, roughness . . . ) is tested automatically with no extra measurement, while with usual ellipsometer said test requires a mechanical rotation of the instrument output arm, In a complete operation mode: the complete Mueller matrix (M) of any sample under study, either in transmission or in reflection.

The optimization of the PSG and PSD configurations with respect to error propagation implies that the states generated by the PSG (and those "filtered" by the PSD) are not "simple" ones, such as linear or circular, and thus usual calibration methods are not really adequate. The invention includes therefore an objective calibration process for each of the two types of measurement cited above, said calibration processes being at once accurate, rapid and easy to implement.

To this end, the invention concerns a polarimetric system for analyzing a sample comprising an excitation section emitting a light beam, said excitation section comprising a polarization state generator containing a polarizer linearly polarizing the incident light beam along a direction of polarization (i), an analysis section comprising a polarization state detector containing an analyzer, and detection means, a processing unit.

According to the invention, the polarization state generator (PSG) comprise a first and a second liquid crystal elements $LC_j$ (j=1, 2) having, for each $LC_j$ element of the PSG an extraordinary axis making an angle $\theta_j$ with respect to the direction of polarization (i) and a retardation $\delta_j$ between its ordinary and extraordinary axes. Said liquid crystal (LCs) elements are placed after the polarizer and are equivalent to electrically controlled retardation plates, the polarization state detector (PSD) comprise a first and a second liquid crystal elements $LC_j$ (j=1, 2) having, for each $LC_j$ element of the PSD an extraordinary axis making an angle $\theta'_j$ with respect to the direction of polarization (i) and a retardation $\delta'_j$ between its ordinary and extraordinary axes. Said liquid crystal $LC_j$ elements equivalent to electrically controlled retardation plates are positioned in reverse order in the PSD with respect to the $LC_j$ elements of the PSG.

According to various embodiments, the present invention also concerns the characteristics below, considered individually or in all their technical possible combinations.

In a first embodiment, the polarization state generator (PSG) and the polarization state detector (PSD) comprise each a first and a second nematic liquid crystal elements $NLC_j$ (j=1, 2). For each $NLC_j$ element of the PSG (respectively, for each $NLC_j$ element of the PSD), the extraordinary axis makes a fixed azimuthal angle $\theta_j$ (resp. $\theta'_j$) with respect to the direction of the input polarizer of the PSG, (resp. the output analyzer of the PSD). The retardation $\delta_j$ (resp. $\delta'_j$) between $NLC_j$ ordinary and extraordinary axes is varied by means of an electrical control, The azimuthal angles $\theta'_j$ are equal to $\theta_j$ (j=1, 2) and the retardations $\delta'_j$ are equal to $-\delta_j$ (j=1, 2) (modulo $2\pi$) for simultaneous optimization of the condition numbers s(W) and s(A) of the modulation and analysis matrices.

By means of proper driving voltages, the couple of retardations $(\delta_1, \delta_2)$ takes sequentially the following values: $(\Delta_1,\Delta_1)$, $(\Delta_1,\Delta_2)$, $(\Delta_2,\Delta_1)$, $(\Delta_2,\Delta_2)$, where $\Delta_1$ and $\Delta_2$ verify the formulae (315°+p90°) and (135°+p90°) respectively, where p is the same integer in both formulae, and The angles $\theta_1$ and $\theta_2$ verify the formulae ($\epsilon27°+q90°$) and ($\epsilon72°+r90°$) respectively where $\epsilon=\pm1$ has the same value in both equations while q and r are any integer, with tolerances on the angles $\theta_i$ and on the retardations $\Delta_i$ equal to +−10° and +−20° respectively. With such tolerances, the condition numbers s(A) and s(W) are then always between the maximum value $$\left(\text{equal to } \frac{1}{\sqrt{3}} \approx 0{,}58\right)$$

and 0,3 which implies that the noise in the final matrix M (which is inversely proportional to s(A) and s(W) for a given noise on the raw data B), never exceeds twice its minimum value.

For spectroscopic applications, i.e. for operation at a variable wavelength, a monochromator is placed before the polarizer of the PSG, or after the analyzer of the PSD, and the values of the retardations $(\delta_1, \delta_2)$ are kept within the boundaries specified above by simply tuning the amplitudes of the control voltages according to the wavelength passing through the monochromator. The currently available NLCs can be used from 400 nm to 1500 nm typically.

In an alternative embodiment, the polarization state generator (PSG) and the polarization state detector (PSD) comprise each a first and a second ferroelectric liquid crystal elements $FLC_j$ (j=1,2). For each $FLC_j$ element of the PSG (respectively, for each $FLC_j$ element of the PSD), the retardation $\delta_j$ (resp. $\delta'_j$) between $FLC_j$ ordinary and extraordinary axes is now fixed. For a given set of driving voltages the extraordinary axes of the FLC make a couple of azimuthal angles $(\theta_1,\theta_2)$ (resp. $(\theta'_1,\theta'_2)$) with respect to the direction of the input polarizer of the PSG (resp. the output analyzer of the PSD), and then these angles are set sequentially to $(\theta_1,\theta_2)$, $(\theta_1+45°,\theta_2)$, $(\theta_1,\theta_2+45°)$, $(\theta_1+45°,\theta_2+45°)$, The azimuthal angles $\theta'_j$ are equal to $\theta_j$ (j=1, 2) and the retardations $\delta'_j$ are equal to $-\delta_j$ (j=1, 2) (modulo $2\pi$) for simultaneous optimization of the condition numbers s(W) and s(A) of the modulation and analysis matrices.

The retardations $(\delta_1, \delta_2)$ are given by $\delta_1=80°+−15°$ and $\delta_2=160°+−15°$, while the orientation angles $(\theta_1, \theta_2)$ are given by $\theta_1=67°+−10°$ and $\theta_2=160°+−40°$. With these values and tolerances, the condition numbers s(A) and s(W) are again between the maximum value $$\left(\text{equal to } \frac{1}{\sqrt{3}} \approx 0{,}58\right)$$

and 0,3.

For spectroscopic applications, i.e. for operation at variable wavelengths, as the values of the retardations $(\delta_1, \delta_2)$ are not electrically controllable as for the nematic crystal elements, the condition numbers s(W) and s(A) cannot be kept above 0.3 throughout the visible with a PSG (or a PSD) comprising a linear polarizer and two FLCs only. However, with typical birefringence dispersion of ferroelectric liquid crystals such a broadband optimization of the condition numbers (s(W) and s(A)>0.3 in the whole spectrum covered by currently available FLCs (420–800 nm typically) is achieved by adding to the system another birefringent fixed element (retardation plate). An example of such an optimization is described hereafter, with a quartz plate inserted between the two FLCs. The broadband ferroelectric-based PSG then comprises:

a linear polarizer, set at an orientation angle $\theta=0$, a first ferroelectric liquid crystal, with a retardation $\delta_1=90°+−5°$ at 510 nm, set at an orientation angle $\theta_1=−10°+/−5°$, a quartz plate, providing a retardation $\delta_Q=90°+/−5°$ at 633 nm, set at an orientation angle $\theta_Q=5°+/−5°$, a second ferroelectric liquid crystal, with a retardation $\delta_2=180°+/−15°$ at 510 nm, set at an orientation angle $\theta_2=71°+/−10°$, This polarimetric system is most conveniently coupled with a spectrometer placed after the analyzer of the PSD, and equipped with a multipoint detector (typically a CCD), which allows the polarimetric analysis to be carried out simultaneously in the whole spectral range defined by the currently available FLC elements, and which might be extended in the future with new FLC materials.

Both embodiments described up to now are provided for illustrative purposes only and should not be used to unduly limit the scope of the present invention. For example, the polarimetric system is not limited to the use of NLCs or FLCs in the PSG and the PSD but a variety of devices combining ferroelectric and nematic liquid crystals can also be designed for simultaneous optimization of the condition numbers of the PSG and the PSD.

Said polarimetric systems are ellipsometers,

Said polarimetric systems are Mueller polarimetric systems for analyzing a sample represented by the sixteen coefficients of a Mueller matrix, The light beam emitted by the excitation section is in the spectral range 400–1500 nm for nematic liquid crystals and 420–800 nm for ferroelectric liquid crystals currently available, This spectral range might be extended in the UV or further into the IR with new LC materials with the different embodiments described within the scope of the present invention, The excitation section comprises a monochromator positioned before the polarizer of the PSG, The detection means comprises either a single detector, or a multipoint photosensitive detector, adapted with the processing unit to polarimetric imaging, The multipoint photosensitive detector is a charge coupled detector (CCD), For spectroscopic applications, the detection means may comprise a spectrometer, placed after the analyzer of the PSD, and preferably coupled with a CCD, to achieve polarimetric analysis simultaneously over the entire spectral range, The device can be used both in transmission and in reflection modes.

The invention also concerns a calibration process of a polarimetric system involving the measurement of at least a reference sample in which
one illuminates the sample with a polarized incident light beam emitted by a polarisation state generator (PSG) containing a polarizer, said PSG modulating the light beam polarization,
said sample transmits or reflects a measurement beam,
one detects the measurement beam with an analysis section comprising a polarization state detector (PSD) containing an analyzer and detection means, and
one processes the electrical signals produced by the detection means with a processing unit.

According to the invention,
Said PSG contains a first and a second liquid crystal elements $LC_j$ (j=1, 2) positioned after the polarizer, said $LC_j$ elements having retardations $\delta_j$ between their ordinary and extraordinary axes and said extraordinary axes making angles $\theta_j$ with respect to the polarization direction defined by the linear polarizer so that by varying the retardation $\delta_j$ of each $LC_j$ element for a fixed value of the $\theta_j$ angle, when the LCj elements are nematic LCs, or by switching the orientation angle $\theta_j$ when the LCj elements are ferroelectric LCs, one modulates the incident light beam polarization, the PSG having a modulation matrix (W) that is non singular, Said PSD contains a third and a fourth liquid crystal elements $LC'_j$ (j=1, 2) positioned before the analyser, said $LC'_j$ elements being the same as the $LC_j$ elements of the PSG but positioned in the reverse order, so that by varying the retardation $\delta'_j$ of each element for fixed values of $\theta'_j$ angles $LC'_j$ when the $LC'_j$ are nematic LCs, or by switching the values of angles $\theta'_j$ at fixed $\delta'_j$ when the $LC'_i$ are ferroelectric LCs, one generates a detection matrix (A) for the analysis section, said matrix being non singular and so that for a given set of retardations ($\delta_j$, $\delta'_j$) (j=1, 2), or for a given set of orientation angles ($\theta_j$, $\theta'_j$), one produces a measured quantity ($D_n$) and so that the processing unit produces the raw data matrix B=AMW, where (M) is the Mueller matrix of the sample, The processing unit produces after n=16 of such measurements and suitable data treatment:
in a simplified (ellipsometric) operation mode: the classical ellipsometric angles ($\Psi$, $\Delta$) as well as the overall transmission (or reflection) coefficient $\tau$ characterizing the samples optically equivalent to DR, such as isotropic non depolarizing surfaces measured in reflection. The measurement procedure includes a check of the validity of the description of the sample as a DR without the need of moving any part of the system, while with usual ellipsometers this can be checked only by rotating the analysis arm by 90°,
in a complete (Mueller polarimetric) operation mode: the complete Mueller matrix (M) of any sample, with its sixteen coefficients, Said calibration processes thus comprise:
for the simplified (ellipsometric) operation mode:
for ellipsometric measurements in transmission of samples assumed to be dichroïc retarders (DR), taking a complete measurement of a reference sample consisting of a DR defined by a Mueller matrix ($M_0$) with known parameters $\tau_0$, $\Psi_0$ and $\Delta_0$, said reference sample being propagation in air and ($M_0$) then being the identity matrix ($I_o$), said measurement providing a reference raw data matrix $B_0 = AM_0 W$,
for ellipsometric measurements in reflection of samples assumed to be dichroïc retarders (DR), taking a complete measurement of a reference sample consisting of a DR defined by a Mueller matrix ($M_o$) with known parameters ($\tau_o$, $\Psi_o$, $\Delta_o$), said sample being a metallic mirror or a known sample for a system working in reflection mode (such as a NIST sample made of silicon covered by a known thickness of oxide), said measurement providing a reference raw data matrix $B_o = AM_o W$, a) For the complete (Mueller polarimetric) operation mode of a system working in transmission:
choosing a set of reference samples elements (p) comprising dichroïc retarders with approximately known Mueller matrices ($M_p$), defined by the parameters ($\tau_p$, $\Psi_p$, $\Delta_p$) one of these elements being the identity matrix ($I_o$) describing propagation in air,
for each of the reference samples (p), taking a complete measurement of said sample, set at an orientation angle $\theta_p$, by modulating the incoming light polarization and analyzing the outcoming light polarization, constructing the matrix $(AR(-\theta_p)M_p R(\theta_p)W)$ using the processing unit, this matrix being a product of the detection matrix (A), the Mueller matrix $(R(-\theta_p)M_p R(\theta_p))$ of said element p set at the angle $\theta_p$, with $R(\theta)$ a matrix describing a rotation by an angle $\theta$ about the z axis and the modulation matrix (W),
calculating the product $(AI_o W)^{-1}(AR(-\theta_p)M_p R(\theta_p)W)$ for each reference sample p in order to obtain an experimental matrix ($C_p$) and determining $M_p$, or, more precisely, the values of its parameters $\tau_p$, $\Psi_p$ and $\Delta_p$, independently of the angles $\theta_p$ through the eigenvalues of $C_p$, which are identical to those of $M_p$. This allows a very accurate characterization of each sample in situ, during the calibration itself,
constructing a matrix $(K_{tot}(\theta_p))$ equal to $$\sum_p (H_p(\theta_p)^T H_p(\theta_p))$$

where the matrix $H_p(\theta_p)$ is defined as $H_p(\theta_p)[X] = R(-\theta_p)M_p R(\theta_p)X - XC_p$ where (X) is any real 4×4 matrix, determining the eigenvalues $\lambda_i$ (i=1 to 16) of the $(K_{tot}(\theta_p))$ matrix in order to extract the modulation matrix (W)

that verifies $K_{tot}(W)=0$, the p reference samples being chosen so that one and only one eigenvalue $\lambda_i$ vanishes when the angles $(\theta_p)$ used in the calculation of $K_{tot}(\theta_p)$ are set equal to their actual values during the calibration measurements, while the other eigenvalues $\lambda_j$, being sorted in decreasing order of value, verify $Z=\lambda_{15}/\lambda_1<1$ and the ratio Z is maximised, This is equivalent to determine the modulation matrix W, (together will all the angles $\theta_p$), as the unique solution of the set of matrix equations:

$$M_p(\theta_p)X=XC_p \qquad (8)$$

determining the detection matrix (A) by constructing the product $(AI_oW)(W^{-1})$.

According to various embodiments, the present invention also concerns the characteristics below, considered individually or in all their technical possible combinations.

a set of reference samples comprises
  a linear polarizer set at $\theta_1=0°$ orientation,
  a linear polarizer set at $\theta_2=90°+/-5°$ orientation,
  a retardation plate with a retardation $\delta=110°+/-30°$ set at $\theta_3=30°+/-5°$,
for spectroscopic applications, the retardation plate is an achromatic quarterwave plate.

b) For the complete (Mueller polarimetric) operation mode of a system working in reflection:

choosing a set of reference samples comprising a linear polarizer, defined by its Mueller matrix $M_{pol}$, and a first DR1 and a second DR2 dichroïc retarders, said $DR_i$ having Mueller matrices $(M_i)$, with i=(1, 2) respectively, with approximately known values of the parameters $\tau_i$, $\Psi_i$, $\Delta_i$, with each of the following sequence of elements, taking a measurement by modulating the incoming light polarization and analyzing the outcoming light polarization, the origin of the azimuthal angles $(\theta=0)$ being taken in the plane of incidence, $DR_1$ alone, set at $\theta=0$, yielding a measured matrix $B_1=AM_1W$
  $DR_2$ alone, set at $\theta=0$, yielding a measured matrix $B_2=AM_2W$
  $DR_1$, set at $\theta=0$, and preceded by the polarizer set at an orientation angle $\theta_1$, yielding a measured matrix $B_{p1}=AM_1R(-\theta_1)M_{pol}R(\theta_1)W$, where $R(\theta)$ is a matrix describing a rotation by an angle $\theta$ about the z axis
  $DR_1$, set at $\theta=0$, and followed by the polarizer, set at an orientation angle $\theta_2$, yielding the measured matrix $B_{p2}=AR(-\theta_2)M_{pol}R(\theta_2)M_1W$, Calculating the products $C_1=B_2^{-1}B_1$ and $C_2=B_1B_2^{-1}$ and then the matrices $N_1=M_2^{-1}M_1$ and $N_2=M_1M_2^{-1}$ through their eigenvalues, which are the same as those of $C_1$ and $C_2$.

$N_1$ and $N_2$ have actually the form of the Mueller matrices of DR, which are oriented, by definition, at $\theta=0$.

Calculating the products $C_{p1}=B_2^{-1}B_{p1}=W^{-1}N_1R(-\theta_1)M_{pol}R(\theta_1)W$ and $C_{p2}=B_{p2}B_2^{-1}=AR(-\theta_2)M_{pol}R(\theta_2)N_2A^{-1}$.
  Constructing a 16×16 real matrix $K_1(\theta_1)$ as $K_1(\theta_1) = H_1^TH_1+H_{p1}(\theta_1)^TH_{p1}(\theta_1)$, where, for any real 4×4 real matrix X, $H_1[X]$ and $H_{p1}(\theta_1)[X]$ are defined as $H_1[X]=N_1X-XC_1$ and $H_{p1}(\theta_1)[X]=N_1M_{pol}(\theta_1)X-XC_{p1}$, Determining the modulation matrix W and the orientation angle $\theta_1$ by requiring that $K_1(\theta_1)$ has one vanishing eigenvalue, and W is the vector associated with this vanishing eigenvalue, Constructing a 16×16 real matrix $K_2(\theta_2)$ as $K_2(\theta_2)=H_2^TH_2+H_{p2}(\theta_2)^TH_{p2}(\theta_2)$, where, for any real 4×4 real matrix X, $H_2[X]$ and $H_{p2}(\theta_2)[X]$ are defined as $H_2[X]=C_2X-XN_2$ and $H_{p2}(\theta_2)[X]=C_{p2}X-XM_{pol}(\theta_2)N_2$ Determining the analysis matrix A and the orientation angle $\theta_2$ by requiring that $K_2(\theta_2)$ has one vanishing eigenvalue, and A is the vector associated with this vanishing eigenvalue, reference samples are then chosen according to the following criteria:

the 16×16 real symmetrical matrices $K_1(\theta_1)$ and $K_2(\theta_2)$ will only have one vanishing eigenvalue, if and only if the angles $\theta_1$ and $\theta_2$ used for their evaluation are equal to the azimuthal angles of the polarizers during the calibration measurements, The next eigenvalues are as large as possible, or, more precisely, the ratios $Z=\lambda_{15}/\lambda_1$ of the smallest nonvanishing eigenvalues $(\lambda_{15})$ over the largest $(\lambda_1)$ eigenvalues of $K_1$ and $K_2$ are as large as possible.

According to various embodiments, the present invention also concerns the characteristics below, considered individually or in all their technical possible combinations.

A set of reference samples is
  a linear polarizer set at $\theta_1=45°+/-5°$,
  a linear polarizer set at $\theta_2=-45°+/-5°$, and
  a couple of samples equivalent to a first DR, and a second $DR_2$ dichroïc retarders, both oriented at $\theta=0$ with respect to the incidence plane, with Mueller matrices $M_1$ and $M_2$ such that the products $M_2^{-1}M_1$ and $M_2^{-1}M_1$ are the Mueller matrices of a DR with $\Psi=45°+/-30°$ and $\Delta=90°+/-10$, For spectroscopic applications, said reference samples comprise a metallic mirror, For spectroscopic applications said reference samples comprise an achromatic quarter-wave plate, oriented with one axis in the incidence plane placed before or after a metallic mirror.

The invention also regards two measurement processes providing, after suitable instrument calibration
  in the ellipsometric mode, the parameters $(\tau,\Psi,\Delta)$ of a sample assumed to be a dichroïc retarder (DR),
  in the complete polarimetric mode, the Mueller matrix (M) of any sample Both measurement processes involve, in all cases:
  emitting an incident light beam linearly polarised along a direction of polarisation (i),
  modulating the incident beam polarization,
  sending the modulated incident beam to the sample, and returning a measurement beam,
  collecting the measurement beam through a polarisation analysis section,
  detecting the measurement beam after the polarization analysis section and producing electrical signals forming the raw data matrix B=AMW,
  transmitting the electrical signals to a processing unit, According to the invention,
  modulating the incident beam polarization by means of two liquid crystal elements $LC_j$ (j=1, 2) by varying either the angular orientations $\theta_j$, of the extraordinary axes with respect to the polarization direction (i) of the linear polarizer when the liquid crystals (LCs) comprise ferroelectric LCs (FLCs), or the retardations $\delta_j$ at fixed orientations when the LCs comprise nematic LCs (NLCs), producing measured quantities ($D_n$) by means of an analysis section comprising two liquid crystal elements $LC'_j$ (j=1, 2) by varying the retardation $\delta'_j$ of each element for fixed values of $\theta'_j$ angles when the LCs are NLCs, or the values of the orientation angles $\theta'_j$ for fixed values of retardation $\delta'_j$ (j=1, 2) when the LCs are FLCs, The raw data B are then processed as follows:

in the ellipsometric mode:

calculating the matrix $C=B_0^{-1}B=W^{-1}M_0^{-1}MW$, where $B_0=AM_0W$ is the raw data matrix taken with the calibration sample. The eigenvalues of C are the same as those of $M_0^{-1}M$, which has the same form as the Mueller matrix of a DR. As a result, two of these eigenvalues ($\lambda_{R1}$ and $\lambda_{R2}$) are positive real, while the other two ($\lambda_{c1}$ and $\lambda_{c2}$) are complex conjugates.

deducing the ellipsometric parameters ($\tau$, $\Psi$, $\Delta$) of the studied sample from these eigenvalues and the known parameters $\tau_0$, $\Psi_0$ and $\Delta_0$ of the reference sample according to:

$$\Psi = \arctan\left(\sqrt{\frac{\lambda_{R1}}{\lambda_{R2}}}\tan\Psi_0\right) \quad (4)$$

$$\Delta = \Delta_0 + \frac{1}{2}\text{Arg}\left(\frac{\lambda_{C1}}{\lambda_{C2}}\right) \quad (5)$$

$$\tau = \frac{\tau_0(\lambda_{R1}+\lambda_{R2})\sin^2 2\Psi_0}{(1-\cos 2\Psi_0 \cos 2\Psi)} \quad (6)$$

checking the validity of the description of the sample as a DR from the following relationship $$|\lambda_{C1}|^2=|\lambda_{C2}|^2=\lambda_{R1}\lambda_{R2} \quad (7)$$

which must be obeyed by the eigenvalues of any Mueller matrix describing a DR, as it can be directly seen from eq. (3).

in the complete polarimetric mode:

the Mueller matrix M of any sample is calculated from the raw data matrix B as $M=A^{-1}BW^{-1}$.

BRIEF DESCRIPTION OF THE DRAWINGS

To facilitate further the description of the invention, the following drawings are provided in which.

These drawings are provided for illustrative purposes only and should not be used to unduly limit the scope of the invention.

DESCRIPTION OF THE PREFERRED EMBODIMENT

Figure 1:
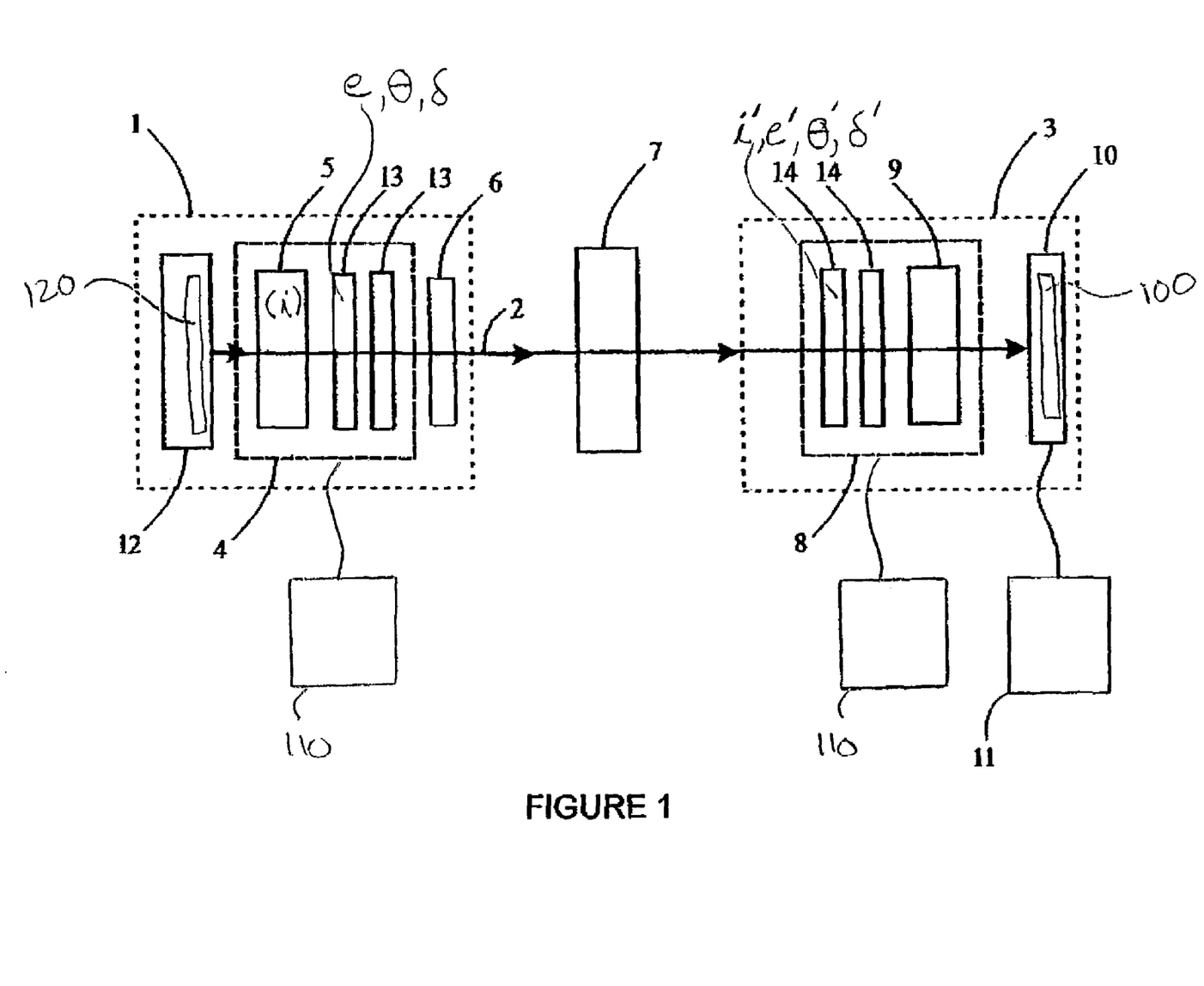
FIG. 1 is a schematic view of a polarimetric system operated in transmission according to the invention.

FIG. 1 shows a polarimetric system according to an embodiment of the invention. It contains an excitation section 1 emitting a light beam 2 and an analysis section 3.

The excitation section 1 comprises a polarization state generator 4 (PSG) through which passes the light beam 2. The polarization state generator 4 comprises a polarizer 5 that linearly polarizes the light beam 2 along a polarization direction (i).

First optical means 6 defines the geometry of the beam 2 at the sample 7.

The analysis section 3 comprises a polarization state detector 8 (PSD) containing an analyzer 9 and detection means 10 for detecting the light beam 2.

In a particular embodiment, the detection means 10 comprises a multipoint photosensitive detector that produces electrical signals sent to a processing unit 11. Said detection means 10 are adapted to polarimetric imaging and the multipoint photosensitive detector is advantageously a charge coupled detector (CCD).

The polarimetric system may comprise as well a monochromator which is located in a first embodiment within the light source 12 that emits the light beam 2, before said beam enters the polarization state generator 4. In a second embodiment, the monochromator is located within the detection means 10, after the light beam exits the polarization state detector 8.

According to the invention, the polarization state generator 4 of the polarimetric system comprises a first and a second liquid crystal elements 13 having birefringent axes, said liquid crystal elements 13 being positioned after the polarizer 5. The polarization state detector 8 also comprises a first and a second liquid crystal elements 14 having birefringent axes and positioned before the analyzer 9. The polarimetric system comprises also control means for controlling said liquid crystal elements 13, 14.

The present invention concerns Mueller polarimetric systems for analyzing samples represented by the sixteen coefficients of a Mueller matrix. The polarization state generator (PSG) 4 and the polarisation state detector (PSD) 8 comprise each a first and a second liquid crystal elements 13, 14 $LC_j$ (j=1, 2) which may either be nematic liquid crystals (NLC) or ferroelectric liquid crystals (FLC).

When NLCs are used, each $NLC_j$ element 13 of the PSG 4 (respectively, for each $NLC_j$ element 14 of the PSD 8), has an extraordinary axis making a fixed angle $\theta_j$ (resp. $\theta'_j$) with respect to the direction of polarisation (i) and a variable retardation $\delta_j$ (resp. $\delta'_j$) between its ordinary and extraordinary axes, which can be controlled electronically, said liquid crystal ($NLC_j$) elements 14 being positioned in reverse order in the PSD 8 with respect to the $NLC_j$ elements 13 of the PSG 4.

When FLCs are used, each $FLC_j$ element 13 of the PSG 4 (respectively, for each $FLC_j$ 14 element of the PSD 8), has a constant retardation $\delta_j$ (resp. $\delta'_j$) between its ordinary and extraordinary axes, and the angle $\theta_j$ (resp. $\theta'_j$) between the extraordinary axis of the FLC and the direction of polarization (i) can be switched between two values separated by 45° by means of an electronic control device. Said liquid crystal ($FLC_j$) elements 14 are positioned in reverse order in the PSD 8 with respect to the $FLC_j$ elements 13 of the PSG 4.

It is known that the application by control means of an appropriate voltage signal on each liquid crystal element (FLC or NLC) 13, 14 allows modulating the polarization of a light beam passing through said liquid crystal elements 13, 14.

In mathematical terms, the liquid crystal elements $LC_j$ 13 of the polarization state generator 4 applies a polarization modulation such that the Stokes vector (S) of the light beam 2 at the exit of the polarization state generator 4 is given by:

$$S = (D^{\delta_2 \theta_2})(D^{\delta_1 \theta_1}) \begin{pmatrix} 1 \\ 1 \\ 0 \\ 0 \end{pmatrix} \quad (8)$$

where $D^{\delta j/\theta j}$ is the Mueller matrix of the $LC_j$ element (j=1,2). When a set of four couples of retardations $(\delta_1, \delta_2)$ or angles $(\theta_1, \theta_2)$ are defined sequentially by the control means of the LCs, four linearly independent Stokes vectors are hence generated from an unpolarized light source.

In a preferred embodiment, the liquid crystal (LC) elements 13 according to the invention are nematic liquid crystal cells (NLC). Said liquid cells are particularly suitable to polarimetric imaging since their typical transmission range is currently between 400 nm and 1500 nm, and could be extended with new liquid crystal materials.

With NLCs and in a preferred embodiment, the orientation angles $\theta'_j$ (j=1,2) are equal to $\theta_j$ (j=1,2) and the retardations $\delta'_j$ (j=1,2) are equal to $-\delta_j$ (j=1,2) (modulo $2\pi$). Advantageously then, the couple of retardations $(\delta_1, \delta_2)$ takes sequentially the following values: $(\Delta_1, \Delta_1)$, $(\Delta_1, \Delta_2)$, $(\Delta_2, \Delta_1)$, $(\Delta_2, \Delta_2)$, where $\Delta_1$ and $\Delta_2$ verify the formulae $(315°+p90°)$ and $(135°+p90°)$ respectively, where p is the same integer in both formulae and the angles $\theta_1$ and $\theta_2$ verify the formulae $(\epsilon 27°+q90°)$ and $(\epsilon 72°+r90°)$ respectively where $\epsilon=\pm 1$ has the same value in both equations while q and r are any integer, with tolerances on the angles $\theta_i$ and on the retardations $\Delta_i$ equal to +−10° and +−20° respectively. This embodiment allows the simultaneous optimization of the condition numbers s(W) and s(A), both A and W matrices being non singular.

The LC elements 13, 14 may also be ferroelectric liquid crystal modulators or any other suitable liquid crystal light modulating device.

With FLCs and in a preferred embodiment, the extraordinary axes of the FLC make a couple of azimuthal angles $(\theta_1, \theta_2)$ (resp. $(\theta'_1, \theta'_2)$) with respect to the direction of the input polarizer 5 of the PSG 4 (resp. the output analyzer 9 of the PSD, and by means of a suitable electronic control device, these angles are set sequentially to $(\theta_1, \theta_2)$, $(\theta_1+45°, \theta_2)$, $(\theta_1, \theta_2+45°)$, $(\theta_1+45°, \theta_2+45°)$. The azimuthal angles $\theta'_j$ are equal to $\theta_j$ (j=1,2) and the retardations $\delta'_j$ are equal to $-\delta_j$ (j=1,2) (modulo $2\pi$) for simultaneous optimization of the condition numbers s(W) and s(A) of the modulation and analysis matrices.

The retardations $\delta_i$ are given by $\delta_1=80°+-15°$ and $\delta_2=160°+-15°$, while the orientation angles $\theta_i$ are given by $\theta_1=67°+-10°$ and $\theta_2=160°+-40°$.

With FLCs and for spectroscopic applications (i.e. operation at variable wavelengths), as the values of the retardations $(\delta_1, \delta_2)$ are not electrically controllable as for nematic liquid crystals, a birefringent plate is preferentially inserted between the two FLCs elements, leading to an overall optimization of A and W matrices in the whole transparency range of the FLCs, which is currently from 420 nm to 800 nm, and might be extended in the future with new materials. With typical values of FLC birefringence dispersion, the retardations $(\delta_1, \delta_2)$ can be advantageously chosen equal to (90°, 180°) in the green part of the spectrum, while the birefringent plate can be chosen as a zero order quarter wave in the red part of the spectrum (633 nm), said plate being made of quartz. Hence, in a particular embodiment and for spectroscopic applications, the birefringent plate is a quartz plate and the PSG 4 comprises:

a linear polarizer, set by definition at an orientation angle $\theta=0$, a first ferroelectric liquid crystal, with a retardation $\delta_1=90°+-5°$ at 510 nm, set at an orientation angle $\theta_1=-10°+-5°$, a quartz plate, providing a (true zero order) retardation $\delta_Q=90°+-5°$ at 633 nm, set at an orientation angle $\theta Q=5°+-5°$, a second ferroelectric liquid crystal, with a retardation $\delta_2=180°+-15°$ at 510 nm, set at an orientation angle $\theta_2=71°+-10°$.

The invention regards as well conventional ellipsometry that is a special case of polarimetry for isotropic layers with smooth interfaces.

Figure 2:
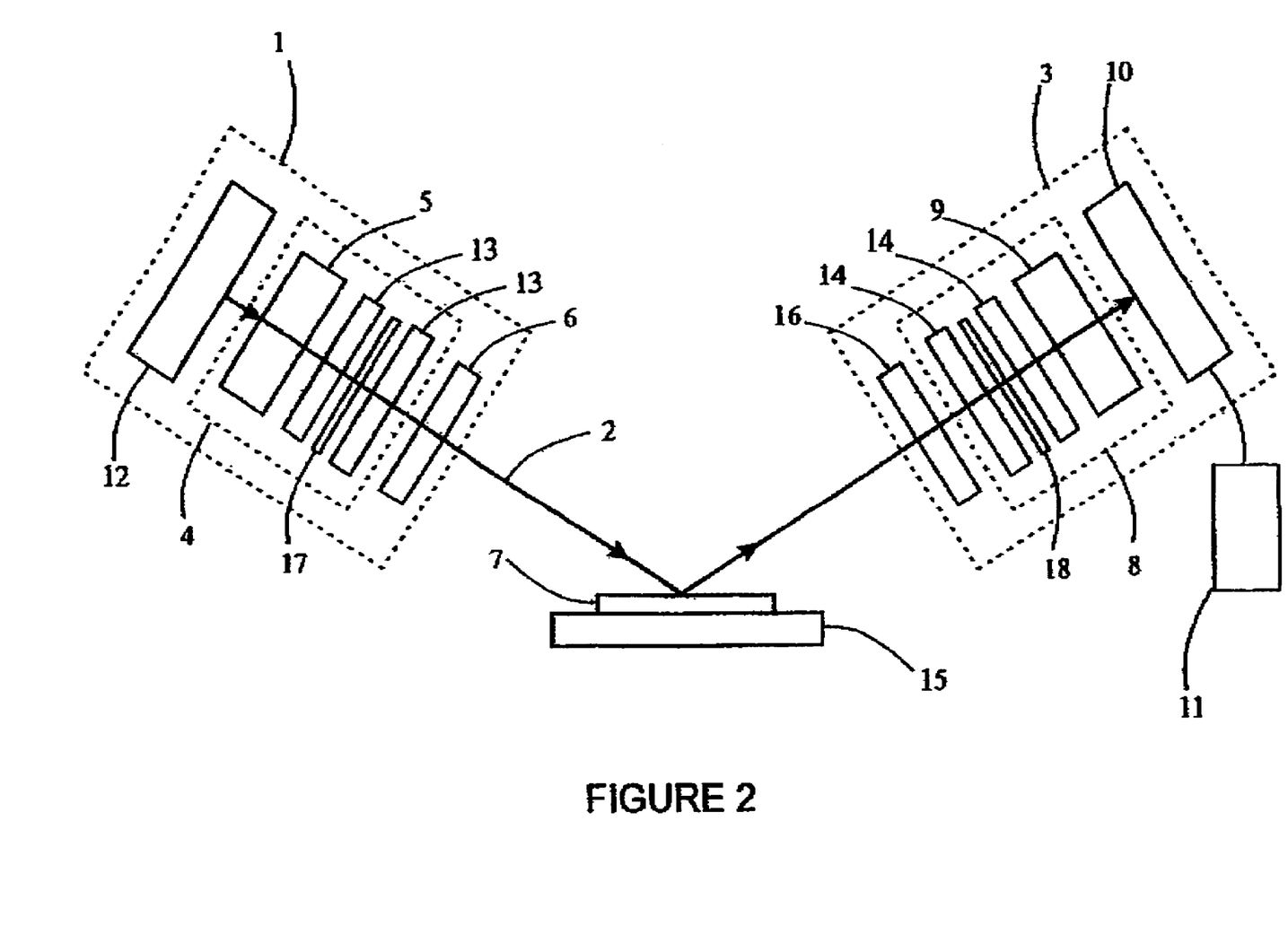
FIG. 2 is a schematic view of a spectroscopic ellipsometric system operated in reflection according to the invention.

FIG. 2 shows a particular embodiment in which a spectroscopic ellipsometric system based on ferroelectric liquid crystals (FLCs) contains an excitation section 1 emitting a light beam 2, a sample holder 15 and an analysis section 3.

The excitation section 1 comprises a polarization state generator 4 (PSG) through which passes the light beam 2. The polarization state generator 4 comprises a polarizer 5 that linearly polarizes the light beam 2 along a polarization direction (i). First optical means 6 focuses the beam 2 at the sample 7.

The incidence angle of the light beam 2 on the sample surface is defined as the angle at which the focused beam strikes the sample surface with respect to the normal to the surface 7. For example, a beam 2 with normal incidence at the sample surface has an incidence angle of zero degree. The angle of incidence of the beam can be advantageously varied. The purpose of the focusing beam is to obtain a small spot on the sample 7, i.e. a compact spot with preferably dimensions inferior to a few tenths of mm². This spot should provide a lateral resolution sufficient to map the sample surface. The light beam 2 emitted by the excitation section 1 is in the transparency spectral region of the FLC, which is currently from 420 to 800 nm, and might be extended further with new FLC materials.

The beam 2 reflects off the sample surface and passes through the analysis section 3. In a more general case, the beam is scattered by the sample surface and passes through the analysis section 3. The analysis section 3 comprises an input optical (collimating) system 16, a polarisation state detector 8 (PSD) containing an analyzer 9 and detection means 10 for detecting the light beam 2. The detection means 10 typically comprises a spectrometer coupled to several photodetectors, typically an array of CCD (charge coupled devices) that produces electrical signals. A processing unit 11 receives said electrical signals.

According to the invention, the polarization state generator 4 of the polarimetric system comprises a first and a second ferroelectric liquid crystal elements 13 having birefringent axes, said liquid crystal elements 13 being positioned after the polarizer 5, and a fixed retardation plate 17, between the two liquid crystal elements 13. The polarization state detector 8 also comprises a first and a second ferroelectric liquid crystal elements 14 having birefringent axes and positioned before the analyzer 9, and a fixed retardation plate 18 set between the FLCs. The polarimetric system comprises also control means for controlling said liquid crystal elements 13, 14.

The present invention can also be advantageously implemented for polarimetric imaging by a CCD camera.

The polarimetric system and the polarimetric measurement process according to the invention have been the object of various implementations whose following example demonstrates the quality of the results obtained.

FIGS. 3 and 4 show the results obtained with a polarimetric system based on nematic liquid crystals, calibrated and operated in transmission, at 633 nm. The test sample was a high quality Babinet-Soleil compensator, which can be considered as dichroïc retarder (DR) with $\Psi \approx 45°$ and a retardation $\Delta$ which is a linear function of the setting of the compensator micrometric screw. The 16 elements of the compensator Mueller matrix (M) were measured for different settings of this screw.

Figure 3A:
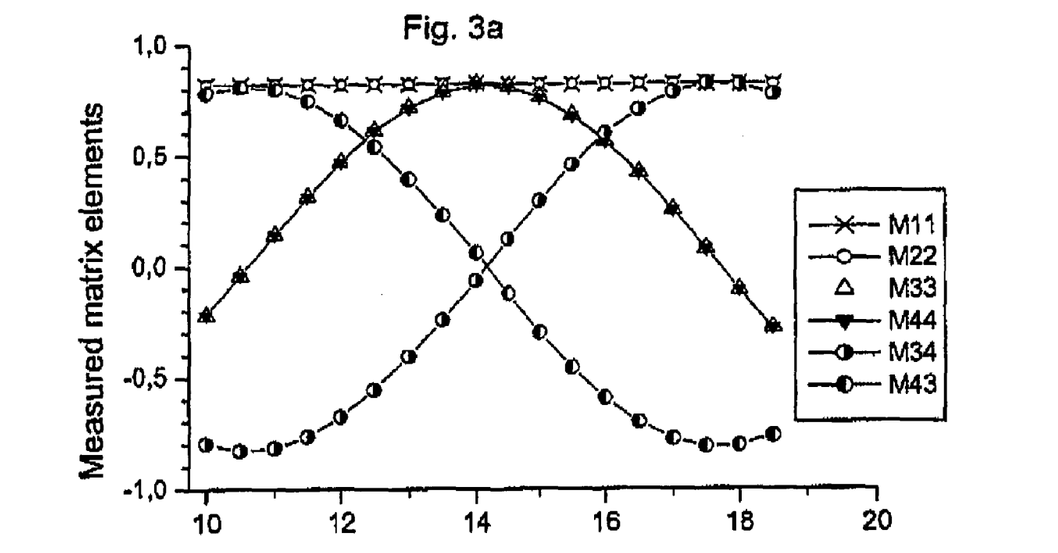
FIG. 3 shows the experimental values of the diagonal block elements of the Mueller matrix of a high quality Babinet-Soleil compensator as a function of the setting x (mm) of the micrometric screw controlling the compensator retardation Δ (FIG. 3a), together with a plot of the values of Δ (deduced from the measured matrix elements according to eqs. (2)) versus the setting x (mm) of the micrometric screw (squares) and the corresponding linear regression (solid line) (FIG. 3b).
Figure 3B:
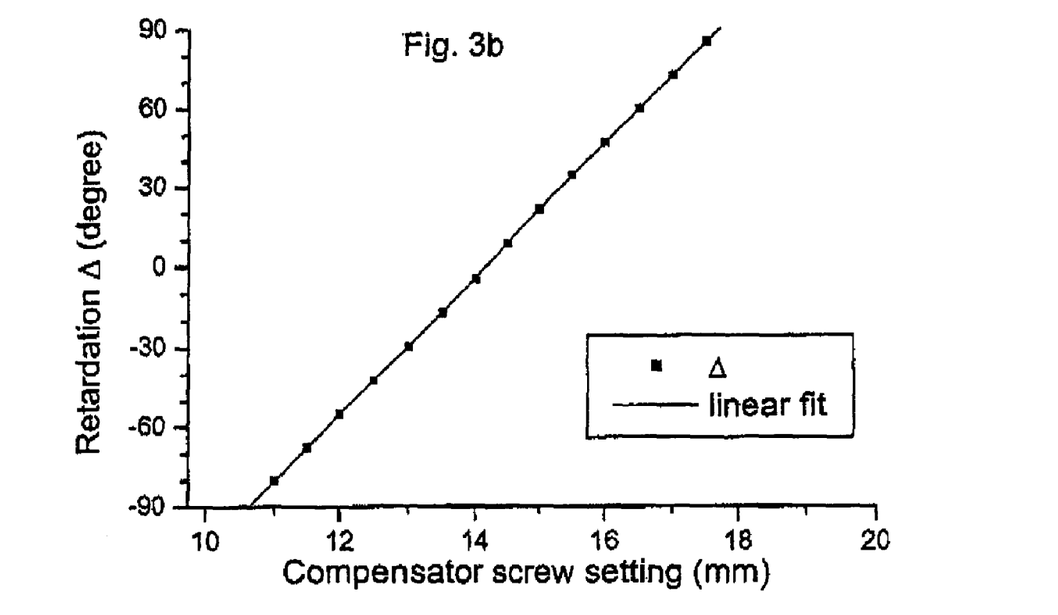

The experimental values for the diagonal block elements are shown on FIG. 3a, versus the screw settings (in mm) of the micrometric screw controlling the compensator retardation $\Delta$; these values follow quite closely (to within 0.01) the behavior expected from eqs. (2) for $\Psi=45°$. In FIG. 3b is shown the variation of the dephasing $\Delta$, as deduced from the values of the lower diagonal block elements, as a function of the screw setting: the standard deviation from a perfect linear fit is 0.13°, equivalent to $\lambda/2700$, which is even better than the accuracy specified by the manufacturer of the compensator, thus confirming the performance of this polarimetric technique.

Figure 4A:
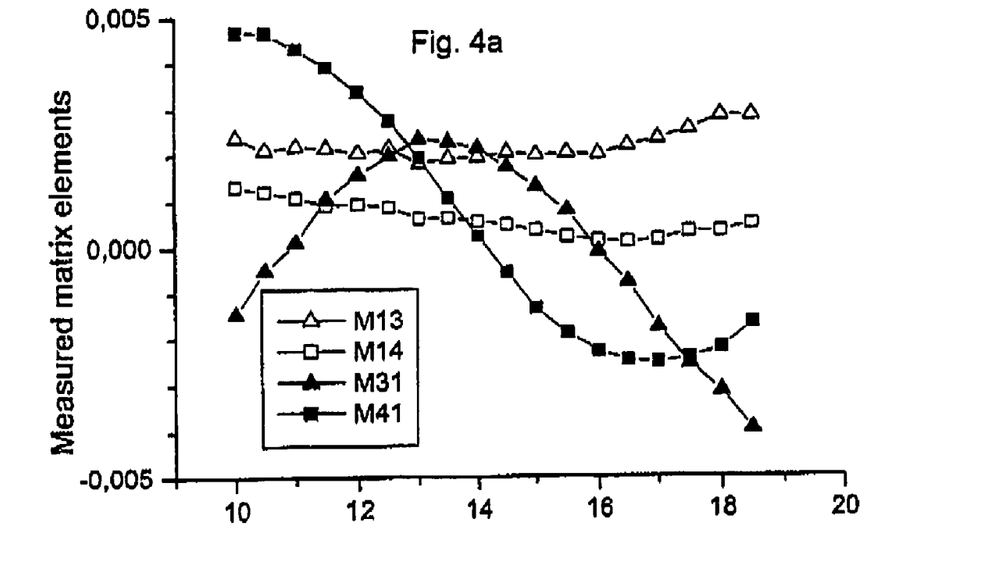
FIG. 4 shows the off diagonal block elements of the same Mueller matrix versus the setting x (mm) of the micrometric screw controlling the compensator retardation Δ.
Figure 4B:
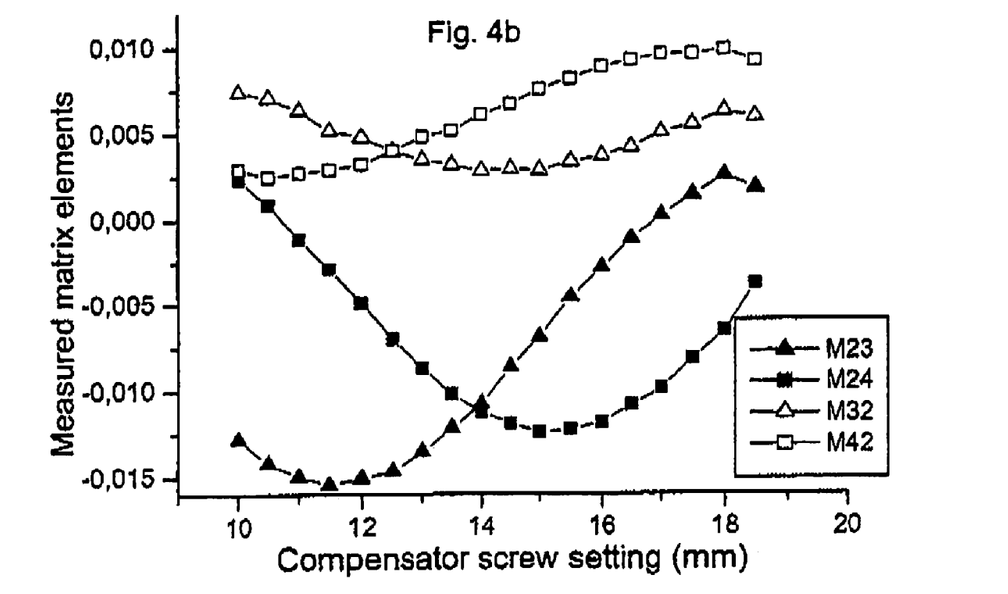

FIG. 4 shows the results obtained for the off-diagonal block elements of the Mueller matrix, again as a function of the micrometric screw setting (in mm). We recall that these elements are expected to vanish. Some of these elements, shown on FIG. 4a, are independent of the compensator orientation, and they are always found to be smaller than $5.10^{-3}$ in absolute value. For the other ones (FIG. 4b) this absolute value can reach $1.5\ 10^{-2}$. This latter value might be due in part to an imperfect alignment of the components within the compensator itself.

The invention claimed is:

1. A polarimetric system for analyzing a sample comprising:
   an excitation section emitting a light beam, said excitation section comprising a polarization state generator containing a polarizer polarizing an incident light beam linearly along a direction of polarization;
   an analysis section comprising a polarization state detector containing an analyzer analysing a light beam linearly along a direction of analysis;
   detection means; and
   a processing unit, wherein,
   said polarization state generator comprises first and second liquid crystal elements, the second liquid crystal element being nearer an exit of the polarization state generator than the first liquid crystal element, each polarization state generator liquid crystal element having i) an extraordinary axis defining an orientation angle with respect to the direction of polarization, and ii) an ordinary axis defining a retardation with respect to the extraordinary axis,
   said polarization state detector comprises first and second liquid crystal elements, the second liquid crystal element being nearer an entry of the polarization state detector than the first crystal element, each polarization state detector liquid crystal element i) an extraordinary axis defining an orientation angle with respect to the direction of polarization, and ii) an ordinary axis defining a retardation with respect to the extraordinary axis,
   the orientation angles of the first and second polarization state generator liquid crystal elements are equal to the orientation angles of the respective first and second polarization state detector liquid crystal elements, and
   the retardations of the first and second polarization state generator liquid crystal elements are equal to minus the retardations of the respective first and second polarization state detector liquid crystal elements, modulo $2\pi$.

2. A polarimetric system according to claim 1, wherein, said liquid crystal elements are nematic liquid crystals, and
   the polarimetric system further comprises an electronic control unit enabling polarization modulation by varying the retardations for the nematic liquid crystals.

3. A polarimetric system according to claim 1, wherein, said liquid crystal elements are ferroelectric liquid crystals, and
   the polarimetric system further comprises an electronic control enabling polarization modulation by varying the orientation angles for the ferroelectric liquid crystals.

4. A polarimetric system according to claim 1, wherein, a couple of the retardations $(\delta_1, \delta_2)$ is varied in a sequence $(\Delta_1, \Delta_1)$, $(\Delta_1, \Delta_2)$, $(\Delta_2, \Delta_1)$, $(\Delta_2, \Delta_2)$,
   where $\Delta_1$ and $\Delta_2$ verify the formulae $\Delta_1=315°+p90°$ and $\Delta_2=135°+p90°$ respectively, where p is the same integer in both formulae, with a tolerance of $+/-20°$,
   the orientations angles verify the formulae $\theta_1=\epsilon27°+q90°$ and $\theta_2=\epsilon72°+r90°$ respectively, where $\epsilon=\pm1$ has the same value in both equations while q and r are any integer, with a tolerance of $+/-10°$.

5. A polarimetric system according to claim 1, wherein, the orientations of the extraordinary axes are set sequentially to $(\theta1, \theta2)$, $(\theta1+45°, \theta2)$, $(\theta1, \theta2+45°)$, $(\theta1+45°, \theta2+45°)$,
   the retardations verify $\delta1=80°+/-15°$ and $\delta2=160°+/-15°$, and
   the orientation angles are given by $\theta1=67°+/-10°$ and $\theta2=160°+/-40°$.

6. A polarimetric system according to claim 5, wherein,
   the polarimetric system is configured for a range of wavelengths,
   a fixed retardation plate is located between said first and second liquid crystal elements in the polarization state, and
   a fixed retardation plate is located between said first and second liquid crystal elements in the polarization state generator.

7. A polarimetric system according to claim 6, wherein, said polarimetric system is optimized for the spectral range from 420 nm to 800 nm, and t
   he retardation plate is a quartz plate, and
   the polarization state generator comprises
   said linear polarizer with the orientation angle set equal to zero,
   said first ferroelectric liquid crystal with the retardation $\delta_1=90°+/-5°$ at 510 nm and the orientation angle set equal to $-10°+/-5°$,
   said quartz retardation plate providing a retardation $\delta_Q=90°+/-5°$ at 633 nm with an orientation angle set equal to $5°+/-5°$, and said second ferroelectric liquid crystal providing a retardation $\delta 2=180°+/-15°$ at 510 nm with an orientation angle set equal to $71°+/-10°$.

8. A polarimetric system according to claim 1, wherein said polarimetric system is an ellipsometer.

9. A polarimetric system according to claim 1, wherein said polarimetric system is a Mueller polarimetric system for analyzing a sample through the measurement of the sixteen coefficients of the sample's Mueller matrix.

10. A polarimetric system according to claim 1, wherein the light beam emitted by the excitation section is in the spectral range 400–1500 nm for nematic liquid crystals, and 420–800 nm for ferroelectric liquid crystals.

11. A polarimetric system according to claim 1, wherein the excitation section comprises a monochromator positioned before the polarization state generator.

12. A polarimetric system according to claim 11, wherein the detection means comprises a monochromator, placed after the polarization state detector.

13. A polarimetric system according to claim 1, wherein the detection means comprises a multipoint photosensitive detector, adapted with the processing unit to polarimetric imaging.

14. A polarimetric system according to claim 13, wherein the multipoint photosensitive detector is a charge coupled detector.

15. A calibration process of a polarimetric system adapted to the complete Mueller polarimetry in transmission of a sample, comprising the steps of:
using a polarimetric system that comprises
i) a polarisation state generator modulating an incident light beam polarization, the generator containing a polarizer, first and second liquid crystal elements positioned after the polarizer, the second liquid crystal element being nearer an exit of the polarization state generator than the first crystal element, each of said liquid crystal elements having a retardation between an ordinary axis and an extraordinary axis and said extraordinary axis making an orientation angle with respect to the polarization direction defined by the linear polarizer, where varying the retardation of each liquid crystal element for a fixed value of the orientation angle, when the liquid crystal elements are nematic liquid crystals or by switching the orientation angle when the liquid crystal elements are ferroelectric LCs, one modulates the incident light beam polarization, the polarization state generator having a nonsingular modulation matrix W, and
ii) a polarization state detector polarization state detector containing an analyzer, detection means, and first and second liquid crystal elements positioned before the analyser, the second liquid crystal element being nearer the entry of the polarization state detector than the first crystal element, each of said liquid crystal elements having a retardation between an ordinary axis and an extraordinary axis and said extraordinary axis making an orientation angle with respect to the direction of analysis of the analyser, said liquid crystal elements being the same as the liquid crystal elements of the polarization state generator, so that by varying the retardation of each liquid crystal element for fixed values orientation angles when the liquid crystals are nematic liquid crystals, or by switching the values of orientation angles for fixed retardation when the liquid crystals are ferroelectric liquid crystals, one generates a non-singular detection matrix A;
choosing a set of reference sample elements comprising dichroic retarders with approximately known Mueller matrices, defined by the parameters $\tau_p$, $\Psi_p$ and $\Delta_p$, one of the reference sample elements being the identity matrix $I_o$ representing propagation in air; and
for each of the reference sample elements taking a complete measurement of said reference sample element set at an orientation angle by
i) illuminating said each reference sample element with said polarized incident light beam emitted by said polarization state generator,
ii) detecting a measurement beam transmitted by said each reference sample element with an analysis section comprising said polarization state detector and said detection means, so that for a given set of retardationsor for a given set of orientation angles one produces a measured quantity;
iii) processing the electrical signals produced by the detection means in accordance with the measured quantity with a processing unit to construct the matrix $(AR(-\theta_p)M_pR(\theta_p)W)$, this matrix being a product of the detection matrix A, the Mueller matrix $R(-\theta_p)M_pR(\theta_p)$ of said reference sample element set at the angle $\theta_p$, with $R(\theta)$ a matrix describing a rotation by an angle $\theta$ about the z axis and the modulation matrix W,
iv) calculating the product $(AI_oW)^{-1}(AR(-\theta_p)M_pR(\theta_p)W)$ for each reference sample element in order to obtain an experimental matrix $C_p$,
v) determining the actual values of $\tau_p$, $\Psi_p$ and $\Delta_p$, and thus the matrix $M_p$, independently of the angles $\theta_p$, from eigenvalues of the experimental matrix $C_p$,
vi) constructing a matrix $(K_{tot}(\theta_p))$ equal to $$\sum_p (H_p(\theta_p)^T H_p(\theta_p))$$

where the matrix $H_p(\theta_p)$ is defined as $H_p(\theta_p)[X]=R(\theta_p)M_pR(\theta_p)X-XC_p$ where X is any real 4×4 matrix,
vii) determining eigenvalues $\lambda_{i+1,16}$ of the $K_{tot}(\theta_p)$ matrix in order to extract the modulation matrix W that verifies $K_{tot}(W)=0$, the reference sample element being chosen so that one and only one eigenvalue $\lambda_i$ vanishes when the angles $\theta_p$ used in the calculation of $K_{tot}(\theta_p)$ are set equal to their actual values during the calibration measurements, while the other eigenvalues $\lambda_j$, being sorted in decreasing order of value, verify $Z=\lambda_{15}\lambda_1<1$ and the ratio Z is maximised,
viii) determining the angles $\theta_p$ by requiring one of the eigenvalues $K_{tot}(\theta_p)$ to vanish, W being the associated eigenvector, and
ix) determining the detection matrix A by constructing the product $(AI_oW)(W^{-1})$.

16. A calibration process according to claim 15, wherein a set of reference sample elements comprises:
a linear polarizer set at $\theta_1=0°$ orientation,
a linear polarizer set at $\theta_2=90°+/-5°$ orientation, and
a retardation plate with a retardation $\delta=110°+/-30°$ set at $\theta_3=30°+/-5°$.

17. A calibration process according to claim 16, wherein the retardation plate is an achromatic quarterwave plate.

18. A calibration process of a polarimetric system adapted to the complete Mueller polarimetry in reflection of a sample, comprising the steps of:
using polarimetric system comprising a polarisation state generator modulating an incident light beam polarization, containing a polarizer, a first and a second liquid crystal elements positioned after the polarizer, the second liquid crystal element being nearer the exit of the polarization state generator than the first crystal element, each of said liquid crystal element having a retardation $\delta_{j=1,2}$ between an ordinary axis and an extraordinary axis and said extraordinary axis making an angle $\theta_{j=1,2}$ with respect to the polarization direction defined by the linear polarizer, where, by varying the retardation $\delta_j$ of each liquid crystal element for a fixed value of the angle $\theta_j$, when the liquid crystal elements are nematic liquid crystals, or by switching the orientation angle $\theta_j$ when the liquid crystal elements are ferroelectric liquid crystals, one modulates the incident light beam (2) polarization, the polarization state generator having a modulation matrix W that is non singular, and a polarization state detector containing an analyzer, detection means, and first and second liquid crystal elements positioned before the analyser, the second liquid crystal element being nearer the entry of the polarization state detector than the first crystal element, each of said liquid crystal elements having a retardation $\delta'_{j=1,2}$ between an ordinary axis and an extraordinary axis and said extraordinary axis making an angle $\theta'_{j=1,2}$ with respect to the direction of analysis of the analyser, said liquid crystal elements being the same as the liquid crystal elements of the polarization state generator, so that by varying the retardation $\delta'_j$ of each liquid crystal element for fixed values of angles $\theta'_j$ when the liquid crystal are nematic liquid crystals, or by switching the values of angles $\theta'_j$ for fixed $\delta'_j$ when the liquid crystal are ferroelectric liquid crystals, one generates a detection matrix A that is non singular;

choosing a set of reference sample elements comprising a linear polarizer, defined by its Mueller matrix $M_{pol}$, and first and second dichroic retarders, said first and second dichroic retarders having Mueller matrices $M_{i=1,2}$ respectively, with approximately known values of the parameters $\tau_{i=1,2}$, $\Psi_{i=1,2}$ and $\Delta_{i=1,2}$; and for each of the reference sample elements
i) illuminating the reference sample element with the polarized incident light beam emitted by said polarization state generator, ii) detecting a measurement beam reflected by said reference sample element with an analysis section comprising said polarization state detector and detection means so that for a given set of retardations $\delta_j$, $\delta'_j$ or for a given set of orientation angles $\theta_j$, $\theta'_j$, one produces a measured quantity $D_n$; and
iii) processing the electrical signals produced by the detection means in accordance with the measured quantity $D_n$ with a processing unit to produce a raw data matrix B=AMW, where M is the Mueller matrix of the reference sample element, in particular, the origin of the azimuthal angles ($\theta$=0) being taken in the plane of incidence:

$DR_1$ alone, set at $\theta$=0, yielding a measured matrix $B_1=AM_1W$, $DR_2$ alone, set at $\theta$=0, yielding a measured matrix $B_2=AM_2W$, $DR_1$, set at $\theta$=0, and preceded by the polarizer set at an orientation angle $\theta_1$, yielding a measured matrix $B_{p1}=AM_1R(-\theta_1)M_{pol}R(\theta_1)W$, where $R(\theta)$ is a matrix representing a rotation by an angle $\theta$ about the z axis, $DR_1$, set at $\theta$=0, and followed by the polarizer, set at an orientation angle $\theta_2$, yielding the measured matrix $B_{p2}=AR(-\theta_2)M_{pol}R(\theta_2)M_1W$;

calculating the products $C_1=B_2^{-1}B_1$ and $C_2=B_1B_2^{-1}$ and then the matrices $N_1=M_2^{-1}M_1$ and $N_2=M_1M_2^{-1}$ through their eigenvalues, which are the same as those of $C_1$ and $C_2$;

calculating the products $C_{p1}=B_2^{-1}B_{p1}=W^{-1}N_1R(-\theta_1)M_{pol}R(\theta_1)W$ and $C_{p2}=B_{p2}B_2^{-1}=AR(-\theta_2)M_{pol}R(\theta_2)N_2A^{-1}$;

defining a $K_1$ matrix as $K_1(\theta_1)[X]=H_1^TH_1 \ldots H_{p1}(\theta_1)^TH_{p1}(\theta_1)$, where, for any 4×4 real matrix X, $H_1[X]$ and $H_{p1}(\theta_1)[X]$ are defined as $H_1[X]=N_1X-XC_1$ and $H_{p1}(\theta_1)[X]=N_1R(-\theta_1)M_{pol}R(\theta_1)X-XC_{p1}$;

determining the modulation matrix W and the orientation $\theta_1$ by requiring that $K_1(\theta_1)$ has one vanishing eigenvalue, and W is the eigenvector associated with this vanishing eigenvalue;

determining similarly the analysis matrix A as the eigenvector associated with the unique vanishing eigenvalue of the matrix $K_2(\theta_2)[X]=H_2^TH_2 \ldots H_{p2}(\theta_2)^TH_{p2}(\theta_2)$ where for any real 4×4 matrix X $H_2[X]=C_2X-XN_2$, $H_{p2}(\theta_2)[X]=C_{p2}X-XR(-\theta_2)M_{pol}R(\theta_2)N_2$; and choosing said reference sample elements according to the following criteria:

the 16×16 real symmetrical matrices $K_1(\theta_1)$ and $K_2(\theta_2)$ will only have one vanishing eigenvalue, if and only if the angles $\theta_1$ and $\theta_2$ used for their evaluation are equal to the azimuthal angles of the polarizers during the calibration measurements, and the next eigenvalues are as large as possible with the ratios $Z=\lambda_{15}\lambda_1$ of the smallest nonvanishing eigenvalues ($\lambda_{15}$) over the largest ($\lambda_1$) eigenvalues of $K_1$ and $K_2$ are as large as possible.

19. A calibration process according to claim 18, wherein the set of reference sample elements comprises:

a linear polarizer set at $\theta_1$=45°+/−5° a linear polarizer set at $\theta_2$=−45°+/−5°, and a couple of reference sample elements equivalent to a first dichroic retarder and a second dichroc retarder, both retarders oriented at $\theta$=0 with respect to the incidence plane, with Mueller matrices $M_1$ and $M_2$ such that the products $M_2^{-1}M_1$ and $M_1^{-1}M_1$ are the Mueller matrices of a DR with $\Psi$=45°+/−30° and $\Delta$=90°+/−10.

20. A calibration process according to claim 19, wherein for a spectroscopic application, said reference sample elements comprise a metallic mirror.

21. A calibration process according to claim 20, wherein for the spectroscopic application, said reference sample elements comprise an achromatic quarterwave plate, oriented with one axis in the incidence plane placed before or after a metallic mirror.

* * * * *